(12) United States Patent
Abedini et al.

(10) Patent No.: US 9,424,532 B1
(45) Date of Patent: Aug. 23, 2016

(54) MACHINE TRAINING AND SEARCH ENGINE FOR PROVIDING SPECIALIZED COGNITIVE HEALTHCARE APPARATUS

(71) Applicant: International Business Machines Corporation, Armonk, NY (US)

(72) Inventors: Mani Abedini, Melbourne (AU); Rajib Chakravorty, Epping (AU); Lida Ghahremanlou, Abbotsford (AU); Shaila Pervin, Docklands (AU); John M. Wagner, Plainville, CT (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 14/976,573

(22) Filed: Dec. 21, 2015

(51) Int. Cl.
  *G06N 99/00*  (2010.01)
  *G06F 19/00*  (2011.01)

(52) U.S. Cl.
  CPC ............ *G06N 99/005* (2013.01); *G06F 19/345* (2013.01)

(58) Field of Classification Search
  CPC .................................................. G06N 99/005
  See application file for complete search history.

(56) References Cited

U.S. PATENT DOCUMENTS

| | | | |
|---|---|---|---|
| 8,024,198 B2 | 9/2011 | Kuo | |
| 2005/0075904 A1 | 4/2005 | Wager et al. | |
| 2009/0083075 A1 | 3/2009 | Henschke et al. | |
| 2010/0088336 A1* | 4/2010 | Johnston, IV ..... | G06F 17/30867 707/770 |
| 2013/0197926 A1 | 8/2013 | Gustafson et al. | |
| 2014/0324450 A1 | 10/2014 | Hicks et al. | |
| 2015/0073943 A1 | 3/2015 | Norris et al. | |
| 2015/0088541 A1 | 3/2015 | Yao | |

OTHER PUBLICATIONS

Duberstein, P. et al., "Influences on patients' ratings of physicians: Physicians demographics and personality", Elsevier, Patient Education and Counseling, 65, Feb. 2007, pp. 270-274.
Goldberg, L., "An Alternative "Description of Personality": The Big-Five Factor Structure", Journal of Personality and Social Psychologs, 1990, vol. 59, No. 6, pp. 1216-1229.
Larson, E. et al., "Clinical Empathy as Emotional Labor in the Patient-Physician Relationship", JAMA, Mar. 2, 2005, vol. 293, No. 9, pp. 1100-1106.
https://watson-api-explorer.mybluemix.net/apis/concept-insights-v2#!/graphs/getRelatedConcepts, "Swagger UI" printed Dec. 4, 2015, pp. 1-58.
https://www.ibm.com/smarterplanet/us/en/ibmwatson/developercloud/doc/qaapi/, "Question and Answer Service Documentation", printed Dec. 4, 2015, pp. 1-4.
https://www.ibm.corn/smarterplanet/us/en/ibmwatson/developercloud/personality-insights.html, "Personality Insight", printed Dec. 4, 2015, pp. 1-4.

* cited by examiner

*Primary Examiner* — Stanley K Hill
*Assistant Examiner* — Ola Olude Afolabi
(74) *Attorney, Agent, or Firm* — Scully, Scott, Murphy & Presser, P.C.; Louis J. Percello, Esq.

(57) ABSTRACT

Training a machine to provide specialized health care apparatus may include receiving text describing a user's health condition via a user interface. Text may be converted into corresponding medical terms. A database may be searched for a list of health care providers treating health conditions associated with the medical terms. A machine learning model may be built that may include user preference for a predefined set of features associated with the user's health condition and health care provider preference for the predefined set of features in treating the user's health condition. The machine learning model may predict one or more of the health care providers that provide treatment for the user's health condition that matches the user's preference. The machine learning model may be retrained based on one or more of feedback from the user, the health care providers, and updated traits of the users and the health care providers.

19 Claims, 4 Drawing Sheets

US 9,424,532 B1

MACHINE TRAINING AND SEARCH ENGINE FOR PROVIDING SPECIALIZED COGNITIVE HEALTHCARE APPARATUS

FIELD

The present application relates generally to computers and computer applications, and more particularly to computer-implement search engines and training a machine through computer-implemented machine learning, for example, for providing specialized cognitive health care apparatus.

BACKGROUND

Encouraging the patient to engage in the treatment process may lead to the improvement of the quality of health care. For instance, if the patient has better understanding of the situation and the treatment options, the patient may become more compliant to the process, leading to more satisfaction on the final result. Statistics show that 10% of all hospital admissions and 23% of nursing home admissions are due to the patient failure to follow the treatment routine. On the other hand, there are evidences that suggest that the participation of the patient in the decision making process can improve the quality life of the patient and bring measurable success in the treatment process.

It has been suggested that empathy (1) makes patients more forthcoming about their symptoms and concerns, thus, facilitating medical information gathering, which, in turn, yields more accurate diagnosis and better care; (2) helps patients regain autonomy and participate in their therapy by increasing their self-efficacy; and (3) leads to therapeutic interactions that directly affect patient recovery (High Extraversion).

Making connections and developing empathy may be fundamental to caring and enhance the therapeutic potential of patient-clinician relationships. However, there are barriers to achieve this, including lack of medical knowledge from patient side, or the fact that some patients are not comfortable having the discussion with their health care providers, e.g., doctors. Sometimes the patient has lack of understanding of the appropriate medical terms of the patient's complaints/issues. Therefore, it becomes difficult to search for the health care providers with relevant specialties matched with the patient's requirement. Even if the patient were able to find the provider with the appropriate specialties, there is often no guarantee beforehand, how comfortable the communication with the selected provider would be in terms of matching personality with the patient. Moreover, it is difficult for the patient to grab the relative information regarding the health problem like how to deal with the medical issue, what the biggest concerns and treatment options are, and what to talk about with the health care provider during the consultation.

Many existing systems try to match patients with physicians by match operations that depend on entities (search terms, such as "location, distance, expertise) and, as a result there is limited or no opportunity for the patients to be aware of how comfortable they would be in communicating with the doctor or with the treatment approach that was suggested by the doctor for the specific ailment and/or health concerns.

It would be beneficial if there were a cognitive solution, which will provide references to relevant information about the problem and prepare the patient for the treatment process, for example, from the early stage of the process.

BRIEF SUMMARY

A computer-implemented method and system of training a machine to provide specialized health care apparatus may be provided. The method, in one aspect, may include receiving text describing a user's health condition via a user interface. The method may also include converting the text into corresponding medical terms. The method may further include searching a database for a list of health care providers treating health conditions associated with the medical terms. The method may also include building a computer-implemented machine learning model comprising user preference for a predefined set of features associated with the user's health condition and health care provider preference for the predefined set of features in treating the user's health condition. The method may further include predicting by the machine learning model one or more of the health care providers that provide treatment for the user's health condition that matches the user's preference. The method may also include receiving feedback from one or more of the user and the health care providers regarding the match. The method may also include modifying the computer-implemented machine learning model based on the feedback to retrain the machine learning model for the predicting.

A system of training a machine to provide specialized health care apparatus, in one aspect, may include one or more hardware processors and one or more memory devices coupled to one or more of the hardware processors. One or more of the hardware processors may be operable to receive text describing a user's health condition via a user interface. One or more of the hardware processors may be further operable to convert the text into corresponding medical terms. One or more of the hardware processors may be further operable to search a database for a list of health care providers treating health conditions associated with the medical terms. One or more of the hardware processors may be further operable to build a machine learning model comprising user preference for a predefined set of features associated with the user's health condition and health care provider preference for the predefined set of features in treating the user's health condition and store the machine learning model on one or more of the memory devices. One or more of the hardware processors may be further operable to run the machine learning model to predict one or more of the health care providers that provide treatment for the user's health condition that matches the user's preference. One or more of the hardware processors may be further operable to receive feedback from one or more of the user and the health care providers regarding the match. One or more of the hardware processors may be further operable to modify the machine learning model based on the feedback to retrain the machine learning model for the predicting.

A computer readable storage medium storing a program of instructions executable by a machine to perform one or more methods described herein also may be provided.

Further features as well as the structure and operation of various embodiments are described in detail below with reference to the accompanying drawings. In the drawings, like reference numbers indicate identical or functionally similar elements.

DETAILED DESCRIPTION

Figure 1:
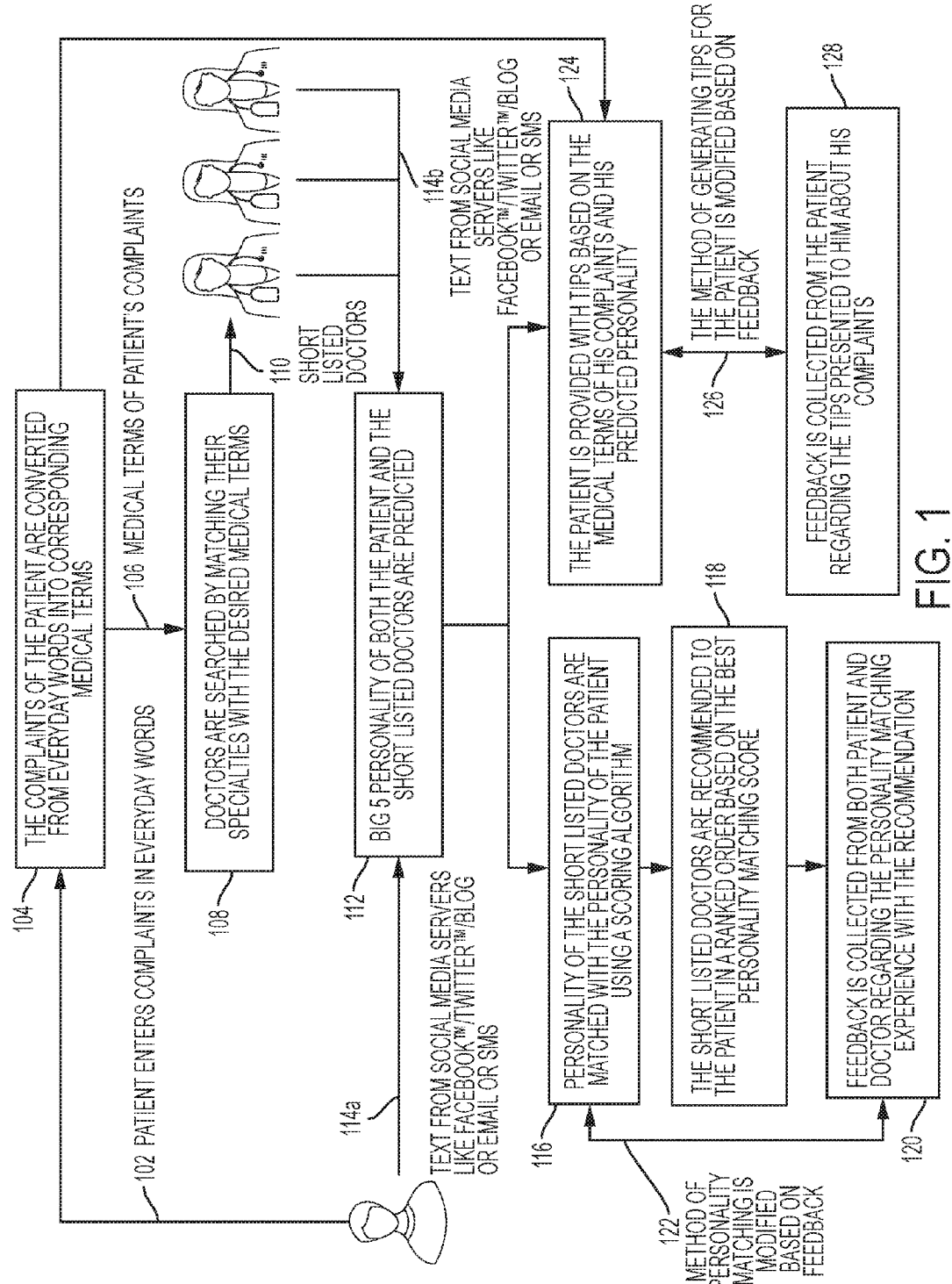
FIG. 1 is a flow diagram illustrating a method of the present disclosure in one embodiment.

A computer-implemented methodology, which may implement a search engine including for example a machine learning component or device, is proposed that provides cognitive care to make the process of searching and communicating with specialized doctors or health care providers easy, for example, for an average patient, and for example, which addresses the above-described problems. In one embodiment, a machine may be trained, using a machine learning technique or algorithm, to provide a personalized and specialized health care apparatus with cognitive care for identifying best matches between doctors and patients. While this disclosure refers to doctors, the description in the present disclosure may apply to physicians and other health care providers.

A methodology of the present disclosure in one embodiment may enable a patient search for the most suitable doctors or healthcare providers faster and with minimal interaction with the search device compared to conventional search process. The methodology of the present disclosure may also provide necessary texts and/or information related to the patient's complaints, which may be useful for discussion during the patient's visit to the doctor.

In one embodiment, a methodology of the present disclosure that may provide a cognitive care solution may look for a doctor suitable for a patient considering the following perspectives simultaneously: 1) The doctor who has the correct expertise pertaining to the patient's complaints, and 2) The doctor and the patient matching in personality, for example, as defined by Big Five factors of personality assessment used in academic psychology.

A methodology of the present disclosure in one embodiment may search for doctors with suitable expertise by converting the non-professional terms given as input by the patient to the appropriate professional terms. In this way, the user does not need any prior knowledge of the corresponding medical expertise needed by a doctor to address the patient complaints. The search engine in one embodiment of the present disclosure also does not require that the user interact with the search engine heavily, for example, only initial description with limited words may suffice. The search engine in one embodiment of the present disclosure may provide for much faster search facility without losing the medical context.

The methodology in one embodiment of the present disclosure may also provide a ranking of the available doctors in order of their match with the patient, for example, based on Big 5 personality profile. For instance, as a result, the patient receives a list of doctors who are compatible with the patient's own personality. In this way, the patients may be more certain and comfortable about discussing complaints with the doctor. The communication between the patient and the doctor can be ensured to be more useful leading to an effective and faster solution.

The methodology in one embodiment of the present disclosure may also provide tips and/or relevant information about the patient's complaints as potential pointer for discussion during the visit to the physician. In this way, the patient is equipped with useful information about the patient's ailment, and has awareness of the patient's ailment, which for example, may be raised during the visit to the physician and potential points of worry, anxiety, and unknowns can be taken care of leading to a more satisfactory health care outcome.

The methodology in one embodiment may perform a "match" operation to select the most suited doctors for a patient in regards to the "treatment philosophy" profile for a specific ailment/health concern. The methodology in one embodiment may consider a number of features defining the "treatment philosophy profile". These features may include, but not limited to, disease controlling or curing, short term or long term solution, surgical or medical treatment, informed or uninformed consent, individual versus (vs.) shared decision, doctor superiority vs. patient empowerment, benefitting or straightforward harshly, and others. The matching may considers variables including medical history and patients' preferred treatment method.

In one embodiment, in a step towards defining treatment philosophy profile, the methodology of the present disclosure, implements a "machine learning" approach to collect these features from each patient and, as a result models patients' preference of doctors. This method enhances the quality and performance of the manual search. For instance, for each person there may be an emphasis on different subset of the "treatment philosophy." Secondly, similar people may prefer the doctors with similar profile. For example, in the current known systems that search for health care providers, a patient has no information about other patients' experience with the health care providers or for specific ailments. Existing feedback mechanism, for example, provided through forums, may not be enough to assess whether the same feedback would apply to the specific patient for example, based on that specific patient's preferences.

The methodology of the present disclosure may be implemented as a search engine incorporating a machine learning technique, and provide improvements to a search engine technology, for example, a web search engine for improving web search engine technology.

FIG. 1 is a flow diagram illustrating a method of the present disclosure in one embodiment. The method may be performed or executed by one or more hardware processors, for example, coupled one or more memory devices, storage devices, and communication interfaces, for communicating to remote computers, via a communication network. At 102, a user, for example, a patient may enter the patient's medical complaint and/or issues, for example, in layperson's expression or text, not necessarily including technical medical terms. For instance, a user interface such as a browser or application specific graphical user interface may be provided and presented to a user on a display device, responsive to the user executing or invoking on one or more hardware computer processors, a search engine or like computer-implemented application or component implementing a methodology of the present disclosure.

At 104, the entered description is converted into corresponding medical terms. For example, description including the term "depression" may be converted to "encephalopathy". For example, computer-implemented natural language processing (NLP) module may parse the description and convert the terms in the description into one or more medical terminologies. As another example, an automated machine learning algorithm may be utilized that can process large volume of text data, connect the meaning of the words and in the process describe an entered description by corresponding medical terms. Such advanced machine learning technique can retrieve additional "concepts" for a given one.

At 106, medical terms of the patient's complaints are transmitted to a computer-implemented searching module. At 108, the searching module searches doctors and generates a list of doctors with appropriate specialties matched with the patient's complaints, for example, shown at 110.

At 112, a computer-implemented personality prediction module automatically searches for obtains texts from social media and/or social network servers, electronic mail (email) servers, short message system (SMS) servers, and other computer servers, text associated with the patient and the doctors in the list (e.g., 110), for example, regarding preferences of the doctors and the patient, for example, as shown at 114*a* and 114*b*. Based on the text or information, the personality prediction module may predict their personality features. The text of preference information about the doctors are patient is obtained according to the authorization or permission given by the respective doctors and patients. For instance, both the patients and the doctors may have given access to the sources of their personalized texts during the registration to the computer-implemented methodology of the present disclosure. For example, only the permitted information may be obtained from the social media or network sources.

In one embodiment, the methodology of the present disclosure in one embodiment may update preference or personality traits regularly without any additional input needed from the user, for example, by considering the updated text from sources, for example, social media server, social network server, email server, other digital text from other like servers.

At 116, personality of the doctors may be matched with the personality of the patient, for example, using a scoring algorithm. For instance, a computer-implemented personality-matching module may run a scoring algorithm to match the personality of the patient with the personality of the listed doctors. At 118, the doctors are recommended to the patient in a ranked order based on the best personality matching score. At 120, for example, after the patient visits the recommended doctor, feedback may be collected from both the patient and the doctor regarding the personality matching experience recommended by the methodology of the present disclosure. Based on the feedback, the personality-matching algorithm may be modified, for example, as shown at 122, as necessary to shape the experience better.

At 124, the patient may be provided with one or more tips on the patient's medical complaints based on the associated medical terms determined at 104 and predicted personality at 112. Systems that use natural language processing to extract information from a supplied document and learn the relevant models to serve the specific purpose may be utilized for providing one or more tips.

At 126, feedback may be collected from the patient regarding the tips presented to the patient about the medical complaints. At 128, the method of generating tips for the patient may be modified based on the feedback to reflect the need of the patient more accurately.

Figure 2:
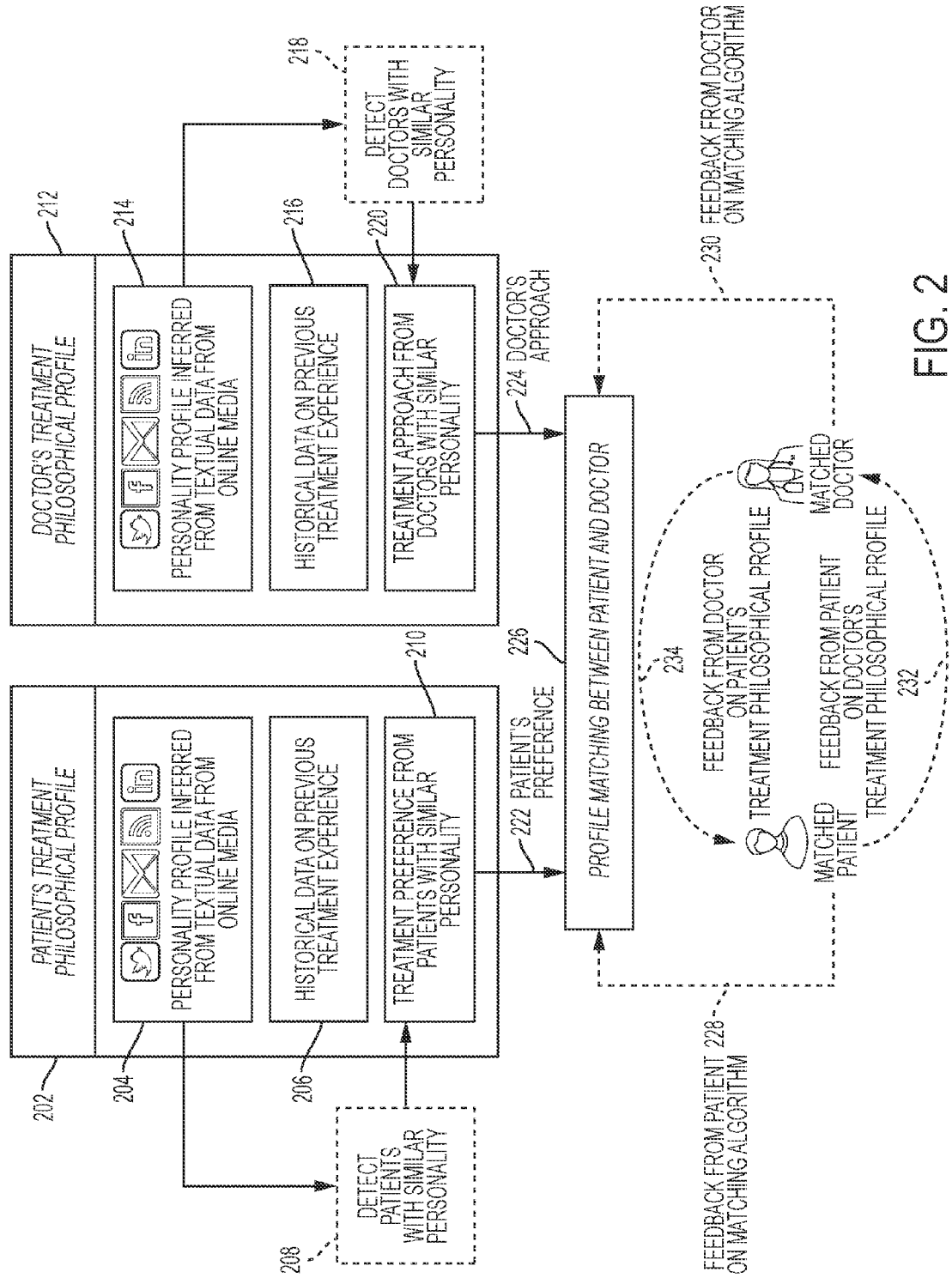
FIG. 2 is a diagram that illustrates creating of treatment philosophical profile and searching for matches based on the treatment philosophical profile in one embodiment of the present disclosure.

FIG. 2 is a diagram illustrating creating of treatment philosophical profile and searching for matches based on the treatment philosophical profile in one embodiment of the present disclosure. An embodiment of the present disclosure generates or develops treatment philosophical profile 202, 212 for both patients and doctors based on patient's preference and doctor's approach towards the treatment regime for a specific health problem and other factors. The various data used in building the treatment philosophical profile may be obtained and used according to the permission or authorization provided by the respective patients and doctors. The methodology of the present disclosure in one embodiment may generate profiles automatically based on natural language, for example, description in everyday words, social media profile, past records, and/or others, for example, using a computer-implemented natural language processing technique.

Historical data on previous treatment experience associated with the patient may be obtained at 206 to build a patient's treatment philosophical profile. In one embodiment, the treatment philosophical profile may be built for both patients and doctors incrementally. For instance, in case of partially built profiles (or not complete profile) of a patient, the methodology of the present disclosure in one embodiment may use similarity and/or clustering methods to find patients with similar personality and augment their preferences and/or approaches to start with. For example, patient preference or personality profile may be inferred from textual data at 206, for example, from various online media, for example, by communicating with social network or social media servers. At 208, based on the textual data from online media obtained at 204, patients with similar preference or personality may be detected, and at 210, treatment preference of those similar patients may be obtained, for example, based on the textual data from online media obtained at 204.

Similarly, at 212 for treatment philosophical profile for doctors may be built, for example, treatment philosophical profile for each doctor in the list of doctors. For example, at 216, historical data on previous treatment experience associated with the doctor may be obtained to build treatment philosophical profile for the doctor. In one embodiment, the treatment philosophical profile may be built incrementally. For instance, in case of partially built profiles (or not complete profile) of a doctor, the methodology of the present disclosure in one embodiment may use similarity and/or clustering methods to find doctors with similar personality and augment their preferences and/or approaches to start with. For example, doctor preference or personality profile may be inferred from textual data at 214, for example, from various online media, for example, by communicating with social network or social media servers. At 218, based on the textual data from online media obtained at 204, doctors with similar preference or personality may be detected, and at 220, treatment preference of those similar doctors may be obtained, for example, based on the textual data from online media obtained at 214.

The methodology of the present disclosure in one embodiment also considers feedback to update the treatment philosophical profile, both for the doctors and the patients. For instance, where a complete profile is absent, the methodology of the present disclosure may use clustering based on personality profiles to find most similar doctors or patients, and augment their treatment philosophy profile. Incrementally, the methodology of the present disclosure may build or complete the profile based on feedback. For example, the patients' feedback can be used to build the doctor treatment philosophy profile and vice versa. In one aspect, treatment philosophical profile of the present disclosure may represent concrete communication of preferences with respect to how the disease should be treated by the two involved parties, e.g., doctors and patients.

With patient and doctor treatment philosophical profiles (222, 224), suitable doctors for a patient's specific health problem may be identified based on the matching between patient's preference and doctor's approach according to their respective treatment philosophical profiles, for example, as shown at 226. The match between patient and doctor at 226 for a specific health problem may be carried out from metrics such as comparing patient's preference 222 and doctor's approach 224 as obtained from the respective treatment philosophical profiles. The match between patient and doctor at 226 for a specific health problem may be determined, for example, by accumulating past feedback on doctor's approaches on the specific health problem from similar patients where similarity is defined on the basis of patient's preference, e.g., as shown at 210 and/or 220. In one embodiment, if available, both the patient's preference and preference of similar patients may be utilized in performing the matching. Similarly, if available, both doctor's preference and preference of similar doctors may be utilized in performing the matching. The matching may output a recommendation list of doctors/physicians. In this way, two individuals may be matched based on a favored method to address the problem in hand, ailments, where the favored method might be one treatment option over another treatment option.

The patient and doctor treatment philosophical profiles may be reconstructed based on feedback, for example, from patients and doctors. The reconstruction may occur, for example after each treatment activity, or periodically after a number of treatment activities. For instance, feedback is collected from both patients and doctors to modify the matching algorithm (228, 230) as well as the treatment philosophical profile of each other (232, 234). Treatment philosophical profile for both patients and doctors may also be reconstructed on regular interval to cater for temporal changes.

The feedback (228, 230, 232, 234) may be collected via any suitable method, for example, web, mobile, other electronic and non-electronic media, from both doctors and patients. The matching at 226 may be performed by a machine learning based matching engine, which may be more and more accurate based on feedback received from both the parties (e.g., doctors and patients). The methodology of the present disclosure may handle feedback in both structured format (e.g., star rating or another structure) and unstructured format (e.g., explained in natural language).

In one embodiment, the methodology of the present disclosure is able to identify the user's current state from the description of symptoms or other objectives from sources such as natural texts or from records, which are usually in natural language format. The methodology of the present disclosure in one embodiment is capable of relating the processed texts to "medical conditions" or "medical preference", both from the doctors' and patients' side, and conduct the search process. This renders the methodology practical to use by both experts and non-experts.

In one embodiment, the methodology of the present disclosure may use the combination of query based approach and automatic rule obtained through techniques such as machine learning algorithms. For instance, a score to the match may be assigned based on all the relevant parameters (treatment philosophical profile) that are available. Such rules can also be updated automatically through feedback from both the patients and doctors.

The machine learning based matching engine, for example, at 226, may continuously learn from previous observations and users and/or doctors' feedback. In this mechanism in one embodiment of the present disclosure, the rule based learning techniques can adopt hierarchical methods that can support complex decision making systems such as treatment philosophy.

The matching engine of the present disclosure may include the ability to provide multi objective decision making process and provide the top matched entities based on the preference of a specific user. For another user with a slightly different preference, the rank list may change despite the fact that the acquired knowledge, rules and philosophical associations stay the same.

The machine learning in one embodiment of the present disclosure may include modelling the preference of a patient for a doctor in treating specific ailment and/or health concern, e.g., the treatment philosophical profile shown with reference to 202 and 212 in FIG. 2. The modelling may include collecting a numeric indicator of the strength of each of the concepts, for example, the features defining the treatment philosophy (e.g., disease controlling or curing, short term or long term solution, surgical or medical treatment, informed or uninformed consent, individual vs. shared decision, doctor superiority vs. patient empowerment, benefiting or straightforward harshly, and others), but not limited to only those features, from patients (and doctors) denoting the importance of that concept when a disease is being treated.

Conceptually, $$P_m^d = [P_{1m}^d, P_{2m}^d, \ldots, P_{Nm}^d]$$

Where $P_m^d$=The preferred strength vector of concepts of m-th patient for the treatment of disease "d"

$P_{im}^d$=The strength of i-th concept for the treatment of disease "d" as preferred by m-th patient N=Number of concepts $$D_n^d = [D_{1m}^d, D_{2m}^d, \ldots, D_{Nm}^d]$$

Where $D_n^d$=The preferred strength vector of concepts of n-th doctors for the treatment of disease "d"

$D_{im}^d$=The strength of i-th concept for the treatment of disease "d" as preferred by n-th doctor N=Number of concepts In addition, a collection of ranking of doctors ranked by patients may provide the ground truth for the "match" operation. These rankings can be obtained in groups such as "High", "Medium" or "Low", in numeric scales (e.g., between 0 and 10) or in other formats.

Conceptually, $R_{m,n}^d$=Ranking given by m-th patient to n-th doctor in treating the disease "d"

Given the vectors, $[P_1^d, P_2^d, \ldots, P_M^d, D_1^d, D_2^d, \ldots, D_D^d]$, machine learning algorithm of the present disclosure in one embodiment builds a model to estimate $[R_{m,n}^d]$, where M=number of patients D=number of doctors The developed model of the present disclosure in one embodiment may be used to rank a doctor n for a particular patient m in treating disease d given the input vector $[p_m^d, D_n^d]$. This can be used to rank more than one doctor and produce a sorted list of preferred doctors.

Machine learning in one embodiment of the present disclosure may also include incorporating new patient and/or doctor into the machine learning built model. For example, the machine learning may include building and updating the treatment philosophical profile and preferences of patients and doctors gradually through the incremental learning process. For instance, once the patient and/or doctor signs up to a system implementing a methodology of the present disclosure, the system can find similar users and/or doctors based on various factors such as personality profiles, preference to treatment approach for different health concerns, using different available media such as social media, text messages, emails, web logs, and others, based on authorized access or permission by the users. With such similarity data, the methodology of the present disclosure in one embodiment may build an initial philosophical treatment profile for the new user (patient or doctor). Over time more interaction and feedback from patients and/or doctors updates the philosophical profiles of the individual.

Figure 3:
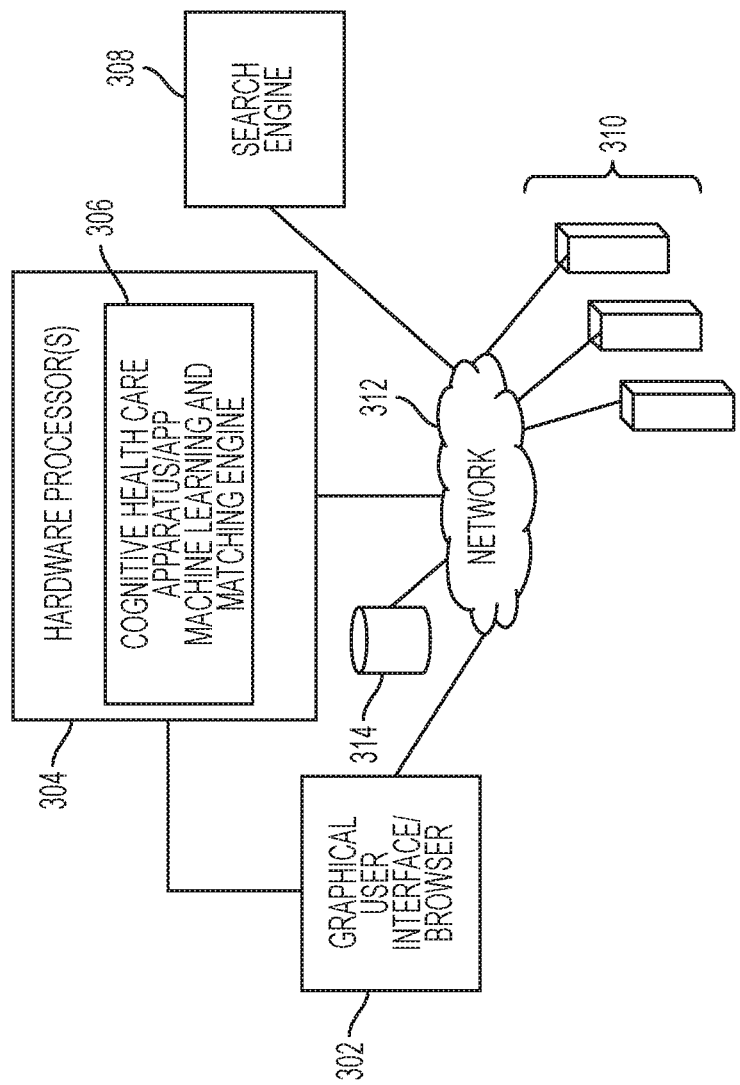
FIG. 3 is a diagram illustrating system components for training a machine to provide specialized health care apparatus in one embodiment of the present disclosure.

FIG. 3 is a diagram illustrating system components for training a machine to provide specialized health care apparatus in one embodiment of the present disclosure. A user interface 302 such as a browser or another graphical user interface may be provided and presented on a user computer, for example, responsive to a user invoking the apparatus or application of the present disclosure in one embodiment. One or more hardware processors 304 may execute the apparatus or application 306 of the present disclosure in one embodiment and perform the processing described herein. The apparatus or application 306 may include a machine learning and matching component or engine 306 as described above with reference to FIGS. 1 and 2. The graphical user interface or browser or the like 302 may be executed via a computer remotely located from the one or more hardware processors 304 over a network 312, or may be executed on the hardware processor 304 locally. One or more hardware processors may receive, for example, via the user interface 302, text describing a user's health condition. One or more of the hardware processors may convert the text into corresponding medical terms, and search a database 312 for a list of health care providers treating health conditions associated with the medical terms. The database 312 for example, may be a medical database that may include a list of health care providers, and accessible by one or more of the hardware processors.

One or more hardware processors 304 may communicate with one or more servers 310 over a computer communications network 312 to obtain data associated with one or more of the user and the health care providers. One or more servers may include, but are not limited to, one or more of social media server, social network server, electronic mail server, and text messaging server. One or more hardware processors 304 may analyse the data to determine preferences of the user and the health care providers, for example, including analyzing for personality traits of the user and the health care providers to determine the preferences. One or more hardware processors 304 may cluster the data into a predefined set of features as related to the user and the health care providers based on the preferences, for example, and build a computer-implemented machine learning model comprising user preference for a predefined set of features associated with the user's health condition and health care provider preference for the predefined set of features in treating the user's health condition. The predefined set of features may include, but are not limited to, disease controlling or curing, short term or long term solution, surgical or medical treatment, informed or uninformed consent, individual vs. shared decision, doctor superiority vs. patient empowerment, and benefiting or straightforward. The machine learning model may be stored on one or more memory devices. One or more hardware processors 304 or the machine learning model (e.g., 306) executing on one or more of the hardware processors may predict a set of health care providers that provide treatment for the user's health condition that matches the user's preference.

One or more hardware processors 304 may also receive feedback from one or more of the user and the health care providers regarding the match. For instance, the user who acted on the recommended doctor, after consulting with the doctor, may provide feedback as to the accuracy of the match. Similarly, a health care provider may invoke a user interface provided in the cognitive health care apparatus 306 to input feedback. One or more hardware processors 304 may modify the machine learning model to retrain the model based on the feedback.

One or more hardware processors 304 may periodically communicating with one or more servers 310 to receive updated data associated with one or more of the user and the health care providers, and continue training the machine learning model further based on the updated data.

In one embodiment, the predefined set of features as related to the user may be determined based on preferences of other users having similar preference profile as the user. Similarly, the predefined set of features as related to one or more of the health care providers may be determined based on preferences of other health care providers having similar preference profile as the one or more of the health care providers. Using profiles of users and/or health care providers with similar traits may be useful, for example, in cases in which the particular user or health care provider's profiles are not yet available, for example, because there is not enough data associated with that particular user or health care provider.

In one embodiment, the cognitive health care apparatus 306 may be implemented as a search engine 308 or augment an existing search engine, for example, a web search engine. The methodology of the present disclosure may extend an existing "search" facility, and for example, in addition to the existing criterion, the concepts and machine learned models can enhance the search process. Further, the methodology of the present disclosure may be integrated with an electronic calendar/appointment/booking system, for example, of both doctors and patients and may provide automated notification. For instance, the search result may be followed by the appointment/booking steps after the patient selects one of the machine generated list of ranked doctors. The methodology of the present disclosure in one embodiment may be also used for informing a decision support system for optimizing resources allocation in data mining.

Figure 4:
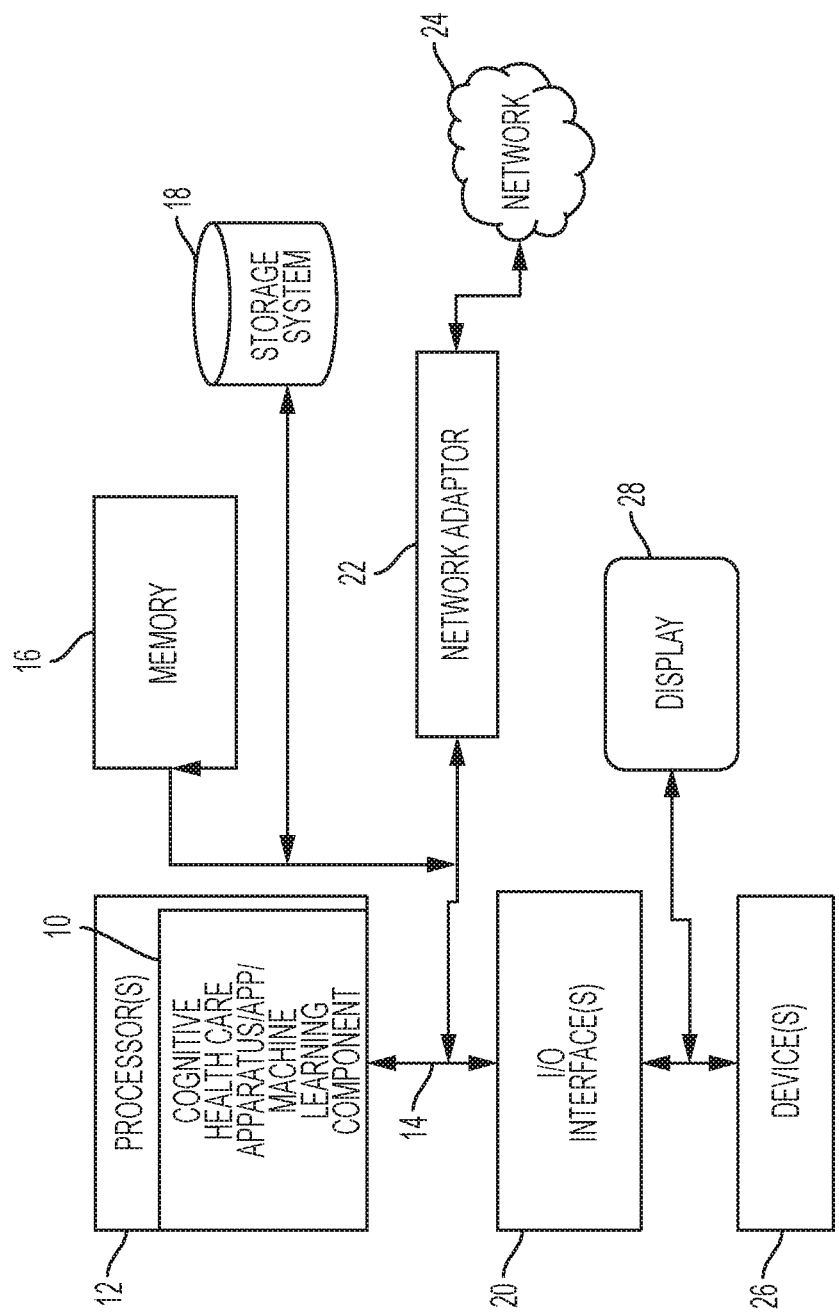
FIG. 4 illustrates a schematic of an example computer or processing system that may implement a cognitive health care system in one embodiment of the present disclosure.

FIG. 4 illustrates a schematic of an example computer or processing system that may implement a cognitive health care system in one embodiment of the present disclosure. The computer system is only one example of a suitable processing system and is not intended to suggest any limitation as to the scope of use or functionality of embodiments of the methodology described herein. The processing system shown may be operational with numerous other general purpose or special purpose computing system environments or configurations. Examples of well-known computing systems, environments, and/or configurations that may be suitable for use with the processing system shown in FIG. 4 may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer system may be described in the general context of computer system executable instructions, such as program modules, being executed by a computer system. Generally, program modules may include routines, programs, objects, components, logic, data structures, and so on that perform particular tasks or implement particular abstract data types. The computer system may be practiced in distributed cloud computing environments where tasks are performed by remote processing devices that are linked through a communications network. In a distributed cloud computing environment, program modules may be located in both local and remote computer system storage media including memory storage devices.

The components of computer system may include, but are not limited to, one or more processors or processing units 12, a system memory 16, and a bus 14 that couples various system components including system memory 16 to processor 12.

The processor 12 may include a cognitive health care and machine learning module 10 that performs the methods described herein. The module 10 may be programmed into the integrated circuits of the processor 12, or loaded from memory 16, storage device 18, or network 24 or combinations thereof.

Bus 14 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system may include a variety of computer system readable media. Such media may be any available media that is accessible by computer system, and it may include both volatile and non-volatile media, removable and non-removable media.

System memory 16 can include computer system readable media in the form of volatile memory, such as random access memory (RAM) and/or cache memory or others. Computer system may further include other removable/non-removable, volatile/non-volatile computer system storage media. By way of example only, storage system 18 can be provided for reading from and writing to a non-removable, non-volatile magnetic media (e.g., a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 14 by one or more data media interfaces.

Computer system may also communicate with one or more external devices 26 such as a keyboard, a pointing device, a display 28, etc.; one or more devices that enable a user to interact with computer system; and/or any devices (e.g., network card, modem, etc.) that enable computer system to communicate with one or more other computing devices. Such communication can occur via Input/Output (I/O) interfaces 20.

Still yet, computer system can communicate with one or more networks 24 such as a local area network (LAN), a general wide area network (WAN), and/or a public network (e.g., the Internet) via network adapter 22. As depicted, network adapter 22 communicates with the other components of computer system via bus 14. It should be understood that although not shown, other hardware and/or software components could be used in conjunction with computer system. Examples include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements, if any, in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

We claim:

1. A computer-implemented method of training a machine to provide specialized health care apparatus, the method performed by one or more hardware processors, comprising:
   receiving text describing a user's health condition via a user interface;
   converting the text into corresponding medical terms;
   searching a database for a list of health care providers treating health conditions associated with the medical terms;
   building a computer-implemented machine learning model comprising user preference for a predefined set of features associated with the user's health condition and health care provider preference for the predefined set of features in treating the user's health condition;
   predicting by the machine learning model one or more of the health care providers that provide treatment for the user's health condition that matches the user's preference;
   receiving feedback from one or more of the user and the health care providers regarding the match; and
   modifying the computer-implemented machine learning model based on the feedback to retrain the machine learning model for the predicting.

2. The method of claim 1, further comprising communicating with one or more servers over a computer communications network to obtain data associated with one or more of the user and the health care providers, wherein the data is clustered into the predefined set of features as related to the user and the health care providers, wherein the computer-implemented machine learning model is built based on the data clustered into the predefined set of features.

3. The method of claim 2, wherein the modifying the computer-implemented machine learning model further comprises periodically communicating with the one or more servers to receive updated data associated with one or more of the user and the health care providers, and wherein the modifying the computer-implemented machine learning model is further based on the updated data.

4. The method of claim 2, wherein the one or more servers comprises one or more of one or more of social media server, social network server, electronic mail server, and text messaging server.

5. The method of claim 1, wherein the predefined set of features as related to the user are determined based on preferences of other users having similar preference profile as the user.

6. The method of claim 1, wherein the predefined set of features as related to one or more of the health care providers are determined based on preferences of other health care providers having similar preference profile as the one or more of the health care providers.

7. The method of claim 1, wherein the predefined set of features comprises disease controlling or curing, short term or long term solution, surgical or medical treatment, informed or uninformed consent, individual vs. shared decision, doctor superiority vs. patient empowerment, and benefiting or straightforward.

8. The method of claim 1, wherein the method is implemented to augment a web search engine.

9. A system of training a machine to provide specialized health care apparatus, comprising:
one or more hardware processors;
one or more memory devices coupled to one or more of the hardware processors,
one or more of the hardware processors operable to receive text describing a user's health condition via a user interface,
one or more of the hardware processors further operable to convert the text into corresponding medical terms,
one or more of the hardware processors further operable to search a database for a list of health care providers treating health conditions associated with the medical terms,
one or more of the hardware processors further operable to build a machine learning model comprising user preference for a predefined set of features associated with the user's health condition and health care provider preference for the predefined set of features in treating the user's health condition and store the machine learning model on one or more of the memory devices,
one or more of the hardware processors further operable to run the machine learning model to predict one or more of the health care providers that provide treatment for the user's health condition that matches the user's preference,
one or more of the hardware processors further operable to receive feedback from one or more of the user and the health care providers regarding the match,
one or more of the hardware processors further operable to modify the machine learning model based on the feedback to retrain the machine learning model for the predicting.

10. The system of claim 9, wherein one or more of the hardware processors communicate with one or more servers over a computer communications network to obtain data associated with one or more of the user and the health care providers, wherein the data is clustered into the predefined set of features as related to the user and the health care providers, wherein the machine learning model is built based on the data clustered into the predefined set of features.

11. The system of claim 10, wherein one or more of the hardware processors modifies the machine learning model by periodically communicating with the one or more servers to receive updated data associated with one or more of the user and the health care providers, wherein the machine learning model is modified based on the on the updated data.

12. The system of claim 10, wherein the one or more servers comprises one or more of one or more of social media server, social network server, electronic mail server, and text messaging server.

13. The system of claim 9, wherein the predefined set of features as related to the user are determined based on preferences of other users having similar preference profile as the user.

14. The system of claim 9, wherein the predefined set of features as related to one or more of the health care providers are determined based on preferences of other health care providers having similar preference profile as the one or more of the health care providers.

15. The system of claim 9, wherein the predefined set of features comprises disease controlling or curing, short term or long term solution, surgical or medical treatment, informed or uninformed consent, individual vs. shared decision, doctor superiority vs. patient empowerment, and benefiting or straightforward.

16. A computer readable storage medium storing a program of instructions executable by a machine to perform a method of training a machine to provide specialized health care apparatus, the method comprising:
receiving text describing a user's health condition via a user interface;
converting the text into corresponding medical terms;
searching a database for a list of health care providers treating health conditions associated with the medical terms;
building a computer-implemented machine learning model comprising user preference for a predefined set of features associated with the user's health condition and health care provider preference for the predefined set of features in treating the user's health condition;
predicting by the machine learning model one or more of the health care providers that provide treatment for the user's health condition that matches the user's preference;
receiving feedback from one or more of the user and the health care providers regarding the match; and
modifying the computer-implemented machine learning model based on the feedback to retrain the machine learning model for the predicting.

17. The computer readable storage medium of claim 16, further comprising communicating with one or more servers over a computer communications network to obtain data associated with one or more of the user and the health care providers, wherein the data is clustered into the predefined set of features as related to the user and the health care providers, wherein the computer-implemented machine learning model is built based on the data clustered into the predefined set of features.

18. The computer readable storage medium of claim 17, wherein the modifying the computer-implemented machine learning model further comprises periodically communicating with the one or more servers to receive updated data associated with one or more of the user and the health care providers, and wherein the modifying the computer-implemented machine learning model is further based on the updated data.

19. The computer readable storage medium of claim 16, wherein the predefined set of features as related to the user are determined based on preferences of other users having similar preference profile as the user and wherein the predefined set of features as related to one or more of the health care providers are determined based on preferences of other health care providers having similar preference profile as the one or more of the health care providers.

* * * * *